US006509293B1

(12) United States Patent
Zoeller et al.

(10) Patent No.: US 6,509,293 B1
(45) Date of Patent: *Jan. 21, 2003

(54) GOLD BASED HETEROGENEOUS CARBONYLATION CATALYSTS

(75) Inventors: Joseph Robert Zoeller, Kingsport, TN (US); Andy Hugh Singleton, Kingsport, TN (US); Gerald Charles Tustin, Kingsport, TN (US); Donald Lee Carver, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/576,628

(22) Filed: May 22, 2000

(51) Int. Cl.$^7$ ............................ B01J 23/02; B01J 23/04; B01J 27/06; B01J 21/08; B01J 23/00
(52) U.S. Cl. ..................... 502/344; 502/184; 502/224; 502/243; 502/317; 502/330; 502/439
(58) Field of Search ................. 502/344, 330, 502/317, 243, 184, 439, 224

(56) References Cited

U.S. PATENT DOCUMENTS

| | | | | |
|---|---|---|---|---|
| 3,626,005 A | * | 12/1971 | Scheben et al. | 260/544 C |
| 3,689,533 A | | 9/1972 | Schultz | |
| 3,717,670 A | | 2/1973 | Schultz | |
| 3,761,513 A | * | 9/1973 | Sennewald et al. | 260/497 A |
| 3,772,380 A | | 11/1973 | Paulik | |
| 3,850,747 A | | 11/1974 | Sinfelt | |
| 3,855,307 A | * | 12/1974 | Rony et al. | 260/604 HF |
| 4,039,572 A | * | 8/1977 | Funakoshi et al. | 260/468 K |
| 4,323,698 A | * | 4/1982 | Haag et al. | 560/233 |
| 4,350,825 A | * | 9/1982 | Huang | 562/406 |
| 4,417,077 A | | 11/1983 | Drago | |
| 4,612,387 A | | 9/1986 | Feitler | |
| 4,625,044 A | * | 11/1986 | Curnutt | 558/277 |
| 4,625,050 A | | 11/1986 | Current | |
| 4,767,574 A | * | 8/1988 | Hanes et al. | 260/410 |
| 4,776,987 A | | 10/1988 | Luft | |
| 4,845,163 A | | 7/1989 | Panster | |
| 4,918,218 A | | 4/1990 | Mueller | |
| 5,004,568 A | * | 4/1991 | Hanes et al. | 260/410 |
| 5,144,068 A | | 9/1992 | Smith | |
| 5,185,462 A | | 2/1993 | Evans | |
| 5,207,878 A | * | 5/1993 | Shimo et al. | 204/157.41 |
| 5,218,140 A | | 6/1993 | Wegman | |
| 5,258,549 A | | 11/1993 | Pimblett | |
| 5,488,143 A | | 1/1996 | Uhm | |
| 5,510,524 A | | 4/1996 | Garland | |
| 5,510,525 A | * | 4/1996 | Sen et al. | 562/542 |
| 5,703,254 A | * | 12/1997 | Gaffney et al. | 549/536 |
| 5,917,089 A | * | 6/1999 | Howard | 562/519 |
| 5,939,569 A | * | 8/1999 | Jones et al. | 549/512 |
| 6,001,768 A | * | 12/1999 | Buysch et al. | 502/230 |
| 6,017,847 A | * | 1/2000 | Wang | 502/331 |
| 6,025,295 A | * | 2/2000 | Tanielyan et al. | 502/154 |
| 6,107,514 A | * | 8/2000 | Nicolau et al. | 560/245 |
| 6,136,746 A | * | 10/2000 | Tanielyan et al. | 502/154 |
| 6,159,896 A | * | 12/2000 | Zoeller et al. | 502/326 |
| 6,177,380 B1 | * | 1/2001 | Zoeller et al. | 502/181 |
| 6,235,673 B1 | * | 5/2001 | Zoeller et al. | 502/159 |

FOREIGN PATENT DOCUMENTS

| | | |
|---|---|---|
| EP | 0 120 631 A1 | 10/1984 |
| EP | 0 461 802 A2 | 12/1991 |
| EP | 0 596 632 A1 | 5/1994 |
| EP | 0 750 406 A1 | 1/1997 |
| EP | 0 759 419 A1 | 2/1997 |
| WO | WO 96/38225 | 12/1996 |

OTHER PUBLICATIONS

Howard, $C_1$ to Acetyls: Catalysis and Process, *Catalysis Today*, (1993), 325–354, 18, Elsevier Science Publishers B.V., Amsterdam.

Fujimoto, Promotion Effect of Hydrogen on Vapor Phase Carbonylation of Methanol over Nickel on Active Carbon Catalyst, *Chemistry Letters*, (1987), 895–898, The Chemical Society of Japan.

Fujimoto, Hydorgen Effects on Nickel–Catalyzed Vapor–Phase Methanol Carbonylation, *Journal of Catalysts*, (1992), 370–382, 133, Academic Press.

Liu, Promoting Effect of Tin on Ni/C Catalyst for Methanol Carbonylation, *Ind. Eng. Chem. Res.*, (1994), 488–492, 33, American Chemical Society.

Yagita, Vapor–Phase Carbonylation of Methanol over Lead on Active Carbon Catalyst, *Catalysis Letters*, (1989), 145–148, 2, J.C. Baltzer AG Scientific Publishing Company.

Maneck, Heterogeneous Carbonylation of Methanol on Rhodium Introduced into Faujasite–Type Zeolites, *Catalysis Today*, (1988), 421–429, 3, Elsevier Science Publishers B.V., Amsterdam.

Gelin, Coordination Chemistry of Rhodium and Iridium in Constrained Zeolite Cavities: Methanol Carbonylation, *Pure & Appl. Chem.*, (1988), 1315–1320, 60, Great Britain.

Krzywicki, Formation and Evolution of the Active Site for Methanol Carbonylation on Oxide Catalysts Containing $RhCl_3$, *Journal of Molecular Catalysts*, ( 1979), 431–440, 6, Elsevier Sequoia S.A., Lausanne, The Netherlands.

Webber, Design and Synthesis of a Solid Bifunctional Polymer Catalyst for Methanol Carbonylation, *Journal of Molecular Catalysts*, (1977), 1–9, 3, Elsevier Sequoia, S.A., Lausanne, The Netherlands.

(List continued on next page.)

Primary Examiner—Stephen S. Silverman
Assistant Examiner—Cam N. Nguyen
(74) Attorney, Agent, or Firm—Susan F. Johnston

(57) ABSTRACT

A solid supported catalyst suitable for the vapor phase carbonylation of lower aliphatic alcohols, ethers, ester, and ester-alcohol mixtures, and desirably, methanol, to produce carboxylic acid, esters and mixtures thereof. The solid supported catalyst includes an effective amount of gold associated with a solid support material in the presence of a halide promoter. Desirably, the support material is selected from carbon, activated carbon, pumice, alumina, silica, silica-alumina, magnesia, diatomaceous earth, bauxite, titania, zirconia, clay, magnesium silicate, silicon carbide, zeolites, ceramics and combinations thereof.

18 Claims, No Drawings

OTHER PUBLICATIONS

Tol, The Hydrogenation of Acetylene in a Pulsed System over Ni and Ir Catalysts, *Catalysis Letters*, (1991), 263–268, 8, J.C. Baltzer A.G. Scientific Publishing Company.

Foger, Skeletal Reactions of Hydrocarbons over Supported Iridium–Gold Catalysts, *Journal of Catalysis*, (1980), 448–463, 64, Academic Press.

Nkosi, Hydrochlorination of Acetylene Using Gold Catalysts: A study of Catalyst Deactivation, *Journal of Catalysis*, (1991), 366–377, 128, Academic Press.

Nkosi, Hydrochlorination of Acetylene Using Carbon–Supported Gold Cataysts: A study of Catalyst Reactivation, *Journal of Catalysis*, (1991), 378–386, 128, Academic Press.

* cited by examiner

GOLD BASED HETEROGENEOUS CARBONYLATION CATALYSTS

FIELD OF THE INVENTION

The present invention relates to a solid phase catalyst and more particularly to a catalyst for the vapor phase carbonylation of alkyl alcohols, ethers and ester-alcohol mixtures to produce esters and carboxylic acids. More particularly, the present invention relates to a supported catalyst which includes an effective amount of gold along with a halogen promoter. The catalyst is particularly useful in the carbonylation of methanol to produce acetic acid, methyl acetate and mixtures thereof.

BACKGROUND OF THE INVENTION

Lower carboxylic acids and esters such as acetic acid and methyl acetate have been known as industrial chemicals for many years. Acetic acid is used in the manufacture of a variety of intermediary and end-products. For example, an important derivative is vinyl acetate, which can be used as monomer or co-monomer for a variety of polymers. Acetic acid itself is used as a solvent in the production of terephthalic acid, which is widely used in the container industry, and particularly in the formation of PET beverage containers.

There has been considerable research activity in the use of metal catalysts for the carbonylation of lower alkyl alcohols, such as methanol, and ethers to their corresponding carboxylic acids and esters, as illustrated in equations 1–3 below:

$$ROH + CO \rightarrow RCOOH \quad (1)$$

$$2ROH + CO \rightarrow RCOOR + water \quad (2)$$

$$ROR + CO \rightarrow RCOOR \quad (3)$$

Carbonylation of methanol is a well-known reaction and is typically carried out in the liquid phase with a catalyst. A thorough review of these commercial processes and other approaches to accomplishing the formation of acetyl from a single carbon source is described by Howard et al. in *Catalysis Today*, 18 (1993) 325–354.

Generally, the liquid phase carbonylation reaction for the preparation of acetic acid using methanol is performed using homogeneous catalyst systems comprising a Group VIII metal and iodine or an iodine-containing compound such as hydrogen iodide and/or methyl iodide. Rhodium is the most common Group VIII metal catalyst and methyl iodide is the most common promoter. These reactions are conducted in the presence of water to prevent precipitation of the catalyst. However, solid heterogeneous carbonylation catalysts offer the potential advantages of easier product separation, lower cost materials of construction, facile recycle, and even higher rates. The use of solid carbonylation catalyst in a vapor phase carbonylation reaction is especially beneficial due to the fact that operating in the vapor phase eliminates catalyst dissolution, i.e., metal leaching from the catalyst support, which occurs in the known heterogeneous processes operating in the presence of liquid compounds.

Rhodium was the first heterogeneous catalyst used in vapor phase carbonylation. Schultz, in U.S. Pat. No. 3,689,533, discloses using a supported rhodium heterogeneous catalyst for the carbonylation of alcohols to form carboxylic acids in a vapor phase reaction. Schultz further discloses the presence of a halide promoter. Schultz in U.S. Pat. No. 3,717,670 goes further to describe a similar supported rhodium catalyst in combination with promoters selected from Groups IB, IIIB, IVB, VB, VIB, VIII, lanthanide and actinide elements of the Periodic Table. Schultz teaches that these elements are useful to promote the rhodium activity, but do not themselves provide carbonylation catalysis. Uhm, in U.S. Pat. No. 5,488,143, describes the use of the alkali metals Li, Na, K, Rb, and Cs, the alkaline earth metals Be, Mg, Ca, Sr, and Ba, or the transition metals Co, Ru, Pd, Pt, Os, Ir, Ni, Mn, Re, Cr, Mo, W, V, Nb, Ta, Ti, Zr, and Hr as promoters for supported rhodium for the halide-promoted, vapor phase methanol carbonylation reaction. Further, Pimblett, in U.S. Pat. No. 5,258,549, teaches that the combination of rhodium and nickel on a carbon support is more active than either metal by itself.

Iridium is also an active catalyst for methanol carbonylation reactions but normally provides reaction rates lower than those offered by rhodium catalysts when used under otherwise similar conditions. In addition to the use of iridium as a homogeneous alcohol carbonylation catalyst, Paulik et al., in U.S. Pat. No. 3,772,380, describe the use of iridium on an inert support as a catalyst in the vapor phase, halogen-promoted, heterogeneous alcohol carbonylation process.

Evans et al., in U.S Pat. No. 5,185,462, describe heterogeneous catalysts for halide-promoted vapor phase methanol carbonylation based on noble metals attached to nitrogen or phosphorus ligands attached to an oxide support.

Nickel on activated carbon has been studied as a heterogeneous catalyst for the halide-promoted vapor phase carbonylation of methanol, and increased rates are observed when hydrogen is added to the feed mixture. Relevant references to the nickel-on-carbon catalyst systems are provided by Fujimoto et al. in *Chemistry Letters* (1987) 895–898 and in *Journal of Catalysis*, 133 (1992) 370–382 and in the references contained therein. Liu et al., in *Ind. Eng. Chem. Res.*, 33 (1994) 488–492, report that tin enhances the activity of the nickel-on-carbon catalyst. Mueller et al., in U.S. Pat. No. 4,918,218, disclose the addition of palladium and optionally copper to supported nickel catalysts for the halide-promoted carbonylation of methanol. In general, the rates of reaction provided by nickel-based catalysts are lower than those provided by the analogous rhodium-based catalysts when operated under similar conditions.

Other single-metals supported on carbon have been reported by Fujimoto et al. in *Catalysis Letters*, 2 (1989) 145–148 to have limited activity in the halide-promoted vapor phase carbonylation of methanol. The most active of these metals is Sn. Following Sn in order of decreasing activity are Pb, Mn, Mo, Cu, Cd, Cr, Re, V, Se, W, Ge and Ga. None of these other single metal catalysts is nearly as active as those based on Rh, Ir, or Ni.

U.S. Pat. No. 5,218, 140, to Wegman, describes a vapor phase process for converting alcohols and ethers to carboxylic acids and esters by the carbonylation of alcohols and ethers with carbon monoxide in the presence of a metal ion exchanged heteropoly acid supported on an inert support. The catalyst used in the reaction includes a polyoxometallate anion in which the metal is at least one of a Group V(a) and VI(a) is complexed with at least one Group VIII cation such as Fe, Ru, Os, Co, Rh, Ir, Ni, Pd or Pt as catalysts for the halide-free carbonylation of alcohols and other compounds in the vapor phase. The process does not utilize a halide cocatalyst.

Various solid support materials have been reported as useful in halide-promoted heterogeneous vapor phase carbonylation systems. European Patent Applications EP 0 120 631 A1 and EP 0 461 802 A2 describe the use of special carbons as supports for carbonylation catalysts having a single transition metal component chosen from Co, Ru, Fe, Ni, Rh, Pd, Os, Ir, Pt, and Group VIII metals. The literature contains several reports of the use of rhodium-containing zeolites as vapor phase alcohol carbonylation catalysts at one bar pressure in the presence of halide promoters. The lead references on this type of catalyst are presented by Maneck et al. in *Catalysis Today*, 3 (1988), 421–429. Gelin et al., in *Pure & Appl. Chem.*, Vol 60, No. 8, (1988) 1315–1320, provide examples of the use of rhodium or iridium contained in zeolite as catalysts for the vapor phase carbonylation of methanol in the presence of halide promoter. Krzywicki et al., in *Journal of Molecular Catalysis*, 6 (1979) 431–440, describe the use of silica, alumina, silica-alumina and titanium dioxide as supports for rhodium in the halide-promoted vapor phase carbonylation of methanol. Luft et al., in U.S. Pat. No. 4,776,987 and in related disclosures, describe the use of chelating ligands chemically attached to various supports as a means to attach Group VIII metals to a heterogeneous catalyst for the halide-promoted vapor phase carbonylation of ethers or esters to carboxylic anhydrides Drago et al., in U.S. Pat. No. 4,417,077, describe the use of anion exchange resins bonded to anionic forms of a single transition metal as catalysts for a number of carbonylation reactions including the halide-promoted carbonylation of methanol.

A number of solid materials have been reported to catalyze the carbonylation of methanol without the addition of the halide promoter. Gates et al., in *Journal of Molecular Catalysis*, 3 (1977/78) 1–9, describe a catalyst containing rhodium attached to polymer bound polychlorinated thiophenol for the liquid phase carbonylation of methanol.

Smith et al., in European Patent Application EP 0 596 632 A1, describe the use of mordenite zeolite containing Cu, Ni, Ir, Rh, or Co as catalysts for the halide-free carbonylation of alcohols. Feitler, in U.S. Pat. No. 4,612,387, describes the use of certain zeolites containing no transition metals as catalysts for the halide-free carbonylation of alcohols and other compounds in the vapor phase.

Certain disadvantages present in the prior art include instability of the carbonylation catalysts, lack of product selectivity and difficult product separation. Therefore, there is a need for an alternative catalyst which can be used in a vapor phase carbonylation process for the production of carboxylic acids and their esters and in which the catalyst is maintained in the solid phase.

SUMMARY OF THE INVENTION

Briefly, the present invention relates to a solid supported catalyst for producing esters and carboxylic acids in a vapor phase carbonylation process and a process for making the catalyst composition. Suitable reactants for contacting the solid catalyst include lower alkyl alcohols, ethers and ester-alcohol mixtures. The catalyst includes a catalytically effective amount of gold. The gold is associated with a solid support material which, desirably, is inert to the carbonylation reaction. The catalyst further includes a halogen promoter.

It is an object of the invention to provide a carbonylation catalyst composition having gold associated with a solid support material.

It is another object of the invention to provide a solid phase catalyst composition for vapor phase carbonylation of methanol to form acetic acid or methyl acetate.

Another object of the invention is to provide a more selective and reactive carbonylation catalyst composition for the production of carboxylic acids.

Yet another object of the invention is to provide a catalyst composition which results in higher yields of acetic acid with minimum formation of ethers, aldehydes, and other undesirable by-products.

These and other objects and advantages of the invention will become apparent to those skilled in the art from the accompanying detailed description.

DETAILED DESCRIPTION OF THE INVENTION

The solid supported catalyst used in the present vapor phase carbonylation process includes a catalytically effective amount of gold associated with a solid support, material, and is further in the presence of a halide promoter. The solid supported catalyst of the present invention is particularly useful in the continuous production of carboxylic acids and esters by reacting lower alkyl alcohols, polyols, ethers, esters or a mixture thereof with carbon monoxide during carbonylation, especially vapor-phase carbonylation. The catalyst of the present invention is particularly useful in a vapor phase carbonylation method for the continuous production of acetic acid, methyl acetate and mixtures thereof.

The examples that follow show that the solid-supported gold catalyst of the present invention is comparable to a heterogeneous solid supported iridium catalyst, when used in a vapor phase carbonylation. It was surprising to find that gold is an effective catalyst since rhodium, iridium, and nickel are the only metals that have previously been disclosed as being active carbonylation catalysts as single metals. It was especially surprising that gold would provide such good catalyst activity since gold has been routinely omitted from the prior disclosure of transition metals useful even as mere promoters of carbonylation catalysts. In fact, gold is considered as being so inert that it is routinely used to line reactor vessels.

In the catalyst of the present invention, a catalytically effective amount of gold is associated with a solid support material that is inert in a carbonylation reaction environment. For clarification of terms used herein, the term "catalytically effective" is used herein to refer to catalysis of the carbonylation of a carbonylatable compound. Further, gold atoms are "associated" with the solid support material when the gold atoms are disposed on, through, and/or near the solid supports as a result of any type of chemical and/or physical relationship.

A material suitable for use as the solid catalyst support material in the present invention is a porous solid having a size of from about 400 mesh per inch to about 0.5 mesh per inch. The shape of the solid support is not particularly important and can be regular or irregular and include extrudates, rods, balls, broken pieces and the like disposed within the reactor.

The support is preferably carbon, or activated carbon, having a high surface area. Activated carbon is well known in the art and may be derived from a variety of sources including coal, peat, and coconut shells having a density of from about 0.03 grams/cubic centimeter (g/cm$^3$) to about 2.25 g/cm$^3$. The carbon can have a surface area of from about 200 square meters/gram (m$^2$/g) to about 1200 m$^2$/g. Other solid support materials may be used, either alone or in combination, in accordance with the present invention include pumice, alumina, silica, silica-alumina, magnesia, diatomaceous earth, bauxite, titania, zirconia, clays, magnesium silicate, silicon carbide, zeolites, ceramics, and combinations thereof.

The compound or form of gold used to prepare the catalyst generally is not critical, and may be selected from any of a variety of compounds containing gold, their respective salts, and mixtures thereof. Particularly useful gold compounds include gold halides, cyanides, hydroxides, oxides, sulfides, and phosphine complexes either alone or in combination. Such materials are available commercially and may be used in the preparation of the catalysts used in the process of the present invention. Gold oxide may be used if dissolved in the appropriate medium. However, the compound used to provide the gold component is preferably in a water-soluble form. Preferred water-soluble gold sources include halides, particularly the tetrahaloaurates. The most preferred hydrogen tetrahaloaurates are hydrogen tetrachloroaurate (III) and hydrogen tetrabromoaurate (III).

The amount of gold on the support can vary from about 0.01 weight percent to about 10 weight percent, with from about 0.1 weight percent to about 2 weight percent being preferred. The weight percent of gold is determined as the weight of gold atoms compared to the total weight of the solid supported catalyst composition.

The catalyst of the present invention is very effective in carbonylation when there are essentially no other metals associated with the support besides gold. It is particularly poignant that the gold catalyst of the present invention is effective even when the catalyst is substantially free of rhodium, iridium, and nickel. "Substantially free" indicates that any presence of rhodium, iridium, or nickel is limited to trace amounts, such as the trace amount of these elements found to be naturally present with gold. However, metals besides gold may be associated with the support as part of the catalyst composition, either as promoters, as co-catalysts, or as inert metals, as long as the amount of gold present is an amount for the gold to effectively catalyze carbonylation in the presence of the other associated metal. If other such metals are associated with the solid support, the ratio of the weight of gold to the weight of the other metal is preferably greater than 1:1, with a ratio of at least about 2:1 being more preferable. Suitable metals for association with the support, besides gold, include alkaline or alkaline earth metals, lanthanides, tin, vanadium, molybdenum, and tungsten. The inventors have found that the lanthanides, tin, and tungsten are the most promising promoting metals for use with the gold catalyst The present solid supported catalyst may be prepared by depositing gold on the solid support material to form a composition wherein a catalytically effective amount of gold is associated with the solid support material. The deposition of gold may be conducted by any means sufficient to cause the gold to associate with the support including but not limited to methods employing heat, electrolyzing, physical embedding, sonification, impregnating, co-precipitation. The preferred method of depositing the gold on the support is by dissolving or dispersing a gold compound in an appropriate solvent, and contacting, preferably impregnating, the support with the gold solution to provide a wet solid support material. The gold atoms are then associated with the support when the solvent is removed by drying the wet support material.

Various methods of contacting the support material with the gold may be employed as long as the contacting method provides association between the gold atoms and the support. For example, a slurry of the gold metal can be poured over or injected into the support material. Alternatively, the support material may be immersed in excess solutions of the active components with the excess being subsequently removed using techniques known to those skilled in the art. The solvent or liquid is evaporated; i.e. the solid support is dried so that at least a portion of the gold is associated with the solid support. Drying temperatures can range from about 100° C. to about 600° C. One skilled in the art will understand that the drying time is dependent upon the temperature, humidity, and solvent. Generally, lower temperatures require longer heating periods to effectively evaporate the solvent from the solid support.

The liquid used to deliver the gold in the form of a solution, dispersion, or suspension is a liquid having a low boiling point, i.e., high vapor pressure at a temperature of from about 10° C. to about 140° C. Examples of suitable solvents include carbon tetrachloride, benzene, acetone, methanol, ethanol, isopropanol, isobutanol, pentane, hexane, cyclohexane, heptane, toluene, pyridine, diethylamine, acetaldehyde, acetic acid, tetrahydrofuran and water.

The carbonylation catalyst of the present invention further includes a halide promoter. The term "halide" is used generically and interchangeably with "halogen", "halide" or "halide containing compound" and includes both the singular or plural forms. It is preferable that the halide is present as a vaporous part of the catalyst composition, thus providing a two-phase catalyst system. However, the halide may also be present as a liquid or as a solid, as long as the halide component is in sufficient contact with the gold component so as to provide gold-halide complex formation. The halide promoter is a catalyst component instead of a reactant, in that it is essentially non-consumed in a reaction, particularly in a carbonylation reaction. The halide may be introduced at the catalyst preparation step or, preferably, is introduced into the carbonylation reactor with the gaseous reactants.

The halide promoter may include one or more of chlorine, bromine and/or iodine compounds and is preferably vaporous under vapor-phase carbonylation conditions of temperature and pressure. Suitable halides include hydrogen halides such as hydrogen iodide and gaseous hydriodic acid; alkyl and aryl halides having up to 12 carbon atoms such as, methyl iodide ethyl iodide, 1-liodopropane, 2-iodobutane, 1-iodobutane, methyl bromide, ethyl bromide, and benzyl iodide. Desirably, the halide is a hydrogen halide or an alkyl halide having up to 6 carbon atoms. Non-limiting examples of preferred halides are hydrogen iodide, methyl bromide and methyl iodide. The halide may also be a molecular halide such as $I_2$, $Br_2$, or $Cl_2$.

The solid supported catalyst of the present invention is most beneficially used in a vapor phase carbonylation process. In such process, the vapor phase carbonylation process of the present invention is conducted by contacting the vapor phase reactants with the catalyst by flowing them through or over the catalyst. This is accomplished by feeding a gaseous mixture comprising the reactants to a carbonylation zone containing the solid supported gold catalyst of the present invention. A gaseous product comprising a carboxylic acid, an ester thereof, or a mixture thereof are recovered from the carbonylation zone. The present heterogeneous vapor-phase process preferably operates entirely in the gas phase, i.e., none of the compounds or materials present in the carbonylation zone or reactor exists in a mobile liquid phase.

Vapor-phase carbonylation is typically operated at temperatures above the dew point of the product mixture, i.e., the temperature at which condensation occurs. However, since the dew point is a complex function of dilution, product composition and pressure, and particularly with respect to non-condensable gases such as unreacted carbon monoxide, hydrogen, or inert diluent gas, the process may still be operated over a wide range of temperatures, provided the temperature exceeds the dew point of the product effluent. In practice, this generally dictates a temperature range of about 100° C. to 500° C., with temperatures in the range of 100° C. to 325° C. being preferred and temperature of about 150° C. to 275° C. being particularly useful.

As with temperature, the useful pressure range is limited by the dew point of the product mixture. However, provided that the reaction is operated at a temperature sufficient to prevent liquefaction of the product effluent, a wide range of pressures may be used, e.g., pressures in the range of about 0.1 to 100 bars absolute. The process preferably is carried out at a pressure in the range of about 1 to 50 bars absolute, most preferably, about 3 to 30 bar absolute.

Suitable feedstock for carbonylation using the present catalyst includes lower alkyl alcohols, ethers, ester and esters-alcohol mixtures which may be carbonylated using the catalyst of the present invention. Non-limiting examples of feedstock include alcohols and ethers in which an aliphatic carbon atom is directly bonded to an oxygen atom of either an alcoholic hydroxyl group in the compound or an ether oxygen in the compound and may further include aromatic moieties. Preferably, the feedstock is one or more lower alkyl alcohols having from 1 to 10 carbon atoms and preferably having from 1 to 6 carbon atoms, alkane polyols having 2 to 6 carbon atoms, alkyl alkylene polyethers having 3 to 20 carbon atoms and alkoxyalkanols having from 3 to 10 carbon atoms. The most preferred reactant is methanol. Although methanol is the preferred feedstock to use with the solid supported catalyst of the present invention and is normally fed as methanol, it can be supplied in the form of a combination of materials which generate methanol. Examples of such materials include (i) methyl acetate and water and (ii) dimethyl ether and water. During carbonylation, both methyl acetate and dimethyl ether are formed within the reactor and, unless methyl acetate is the desired product, they are recycled with water to the reactor where they are converted to acetic acid. Accordingly, one skilled in the art will further recognize that it is possible to utilize the catalyst Of the present invention to produce a carboxylic acid from an ester feed material.

Although the presence of water in the gaseous feed mixture is not essential when using methanol, the presence of some water does serve to suppress formation of methyl acetate and/or dimethyl ether. Therefore, when using methanol to generate acetic acid, the molar ratio of water to methanol can be from about 0:1 to about 10:1, with a range of about 0.01:1 to about 1:1 being preferable. When using an alternative source of methanol such as methyl acetate or dimethyl ether, the amount of water fed usually is increased to account for the mole of water required for hydrolysis of the methanol alternative. Accordingly, when using either methyl acetate or dimethyl ether, the mole ratio of water to ester or ether is in the range of about 1:1 to about 10:1, with a range of about 1:1 to about 3:1 being preferable. In the preparation of acetic acid, it is apparent that combinations of methanol, methyl ester, and/or dimethyl ether are equivalent, provided the appropriate amount of water is added to hydrolyze the ether or ester to provide the methanol reactant.

When the present solid supported catalyst is used in a vapor-phase carbonylation process to produce methyl acetate, no water should be added and dimethyl ether becomes the preferred feedstock. Further, when methanol is used as the feedstock in the preparation of methyl acetate, it is necessary to remove water. However, the primary utility of the catalyst of the present invention is in the manufacture of acetic acid.

In practice, a gaseous mixture having at least one lower alkyl alcohol, ether or ester-alcohol mixture, along with carbon monoxide and a halide, are fed to a reactor carbonylation zone containing the gold supported catalyst described above. The reactant, in the vapor phase, is allowed to contact the solid supported catalyst. The carbonylation zone of the reactor is maintained under carbonylation conditions of temperature and pressure. If acetic acid is the desired product, the feedstock may consist of methyl alcohol, dimethyl ether, methyl acetate, a methyl halide or any combination thereof. If it is desired to increase the proportion of acid produced, the ester may be recycled to the reactor together with water or introduced into a separate reactor with water to produce the acid in a separate zone.

The carbon monoxide can be a purified carbon monoxide or include other gases. The carbon monoxide need not be of a high purity and may contain from about 1% by volume to about 99% by volume carbon monoxide, and preferably from about 70% by volume to about 99% by volume carbon monoxide. The remainder of the gas mixture may include such gases as nitrogen, hydrogen, carbon dioxide, water and paraffinic hydrocarbons having from one to four carbon atoms. Although hydrogen is not part of the reaction stoichiometry, hydrogen may be useful in maintaining optimal catalyst activity. The preferred ratio of carbon monoxide to hydrogen generally ranges from about 99:1 to about 2:1, but ranges with even higher hydrogen levels are also likely to be useful.

The amount of halide present in the gaseous feed to produce an effective carbonylation is based on the amount of alcohol or alcohol equivalents. The molar ratio of alcohol to halide ranges from about 1:1 to about 10,000:1, with the preferred range being from about 5:1 to about 1000:1.

In a preferred aspect of the invention, the vapor-phase carbonylation catalyst of the present invention may be used for making acetic acid, methyl acetate or a mixture thereof. The process includes the steps of contacting a gaseous mixture comprising methanol and carbon monoxide with the gold catalyst described above in a carbonylation zone and recovering a gaseous product from the carbonylation zone. The main gaseous products recovered include methyl acetate, acetic acid, unreacted methanol, and methyl iodide.

The present invention is illustrated in greater detail by the specific examples present below. It is to be understood that these examples are illustrative embodiments and are not intended to be limiting of the invention, but rather are to be construed broadly within the scope and content of the appended claims.

EXAMPLES

In the examples that follow, all of the catalysts were prepared in a similar manner except as specified otherwise.

Preparation of Catalysts

Catalyst 1 (Au on Carbon):

Hydrogen tetrachloroaurate (III) hydrate (50.11% Au, 0.458 grams, 1.16 mmol) was dissolved in 30 mL of distilled water. The solution was then added to 20 grams of 12×40 mesh activated carbon granules (20.0 g, obtained from Calgon) having a BET surface area in excess of 800 m$^2$/g contained in an evaporating dish. The mixture was heated on the steam bath with continuous stirring until it became free flowing and then transferred to a quartz tube measuring 106 cm long by 25 mm outer diameter. The quartz tube containing the mixture was placed in a three-element electric tube furnace so that the mixture was located in the approximate center of the 61 cm long heated zone of the furnace.

Nitrogen (100 standard cubic centimeters per minute) was continuously passed through the catalyst bed, and the tube was heated from ambient temperature to 300° C. over a 2 hour period, held at 300° C. for 2 hours and then allowed to co I back to ambient temperature.

Comparative Catalysts C-1 (Ag on Carbon):

The steps used for preparing Catalyst 1 were repeated, except that silver nitrate (0.198 g, 1.16 mmol) was used in place of the hydrogen tetrachloroaurate trihydrate.

Comparative Catalyst C-2 (Ir on Carbon):

Iridium (III) chloride hydrate (418 mg, 1.17 mmol of Ir) was dissolved in distilled water (30 mL) and then added to 12×40 mesh activated carbon granules (20.0 g, obtained from Calgon) having a BET surface area in excess of 800 $m^2/g$ contained in an evaporating dish. The mixture was heated on the steam bath with continuous stirring until it became free flowing and then transferred to a quartz tube measuring 106 cm long by 25 mm outer diameter. The quartz tube containing the mixture was placed in a three-element electric tube furnace so that the mixture was located in the approximate center of the 61 cm long heated zone of the furnace. Nitrogen (100 standard cubic centimeters per minute) was continuously passed through the catalyst bed, and the tube was heated from ambient temperature to 300° C. over a 2 hour period, held at 300° C. for 2 hours and then allowed to cool back to ambient temperature.

The catalyst prepared in this manner (Catalyst C-2) contained 1.10% Ir and had a density of 0.57 g per mL.

Method used for Carbonylation of Methanol:

The reactor system consisted of a 800 to 950 mm (31.5 and 37 inch) section of 6.35 mm (¼ inch) diameter tubing constructed of Hastelloy alloy. The upper portion of the tube constituted the preheat and reaction (carbonylation) zones which were assembled by inserting a quartz wool pad 410 mm from the top of the reactor to act as support for the catalyst, followed sequentially by (1) a 0.7 g bed of fine quartz chips (840 microns), (2) 0.5 g of one of the catalysts prepared as described in the preceding examples, and (3) an additional 6 g of fine quartz chips. The top of the tube was attached to an inlet manifold for introducing liquid and gaseous feeds.

The six g of fine quartz chips acted as a heat exchange surface to vaporize the liquid feeds. Care was taken not to allow any liquid feeds to contact the catalyst bed at any time, including assembly, start-up, Operation, and shutdown. The remaining lower length of tubing (product recovery section) consisted of a vortex cooler which varied in length depending on the original length of tubing employed and was maintained at approximately 0–5° C. during operation.

The gases were fed using Brooks flow controllers and liquids were fed using a high performance liquid chromatography pump. The gaseous products leaving the reaction zone were condensed using a vortex cooler operating at 0–5° C. The product reservoir was a tank placed downstream from the reactor system. The pressure was maintained using a Tescom 44-2300 Regulator on the outlet side of the reactor system and the temperature of the reaction section was maintained using heating tape on the outside of the reaction system.

Feeding of hydrogen and carbon monoxide to the reactor was commenced while maintaining the reactor at a temperature of 240° C. and a pressure of 17.2 bara (250 psia). The flow rate of hydrogen was set at 25 standard cubic cm. per minute (cc/min) and the carbon monoxide flow rate was set at 100 cc/min. The reactor section was maintained under these conditions for 1 hour or until the temperature and pressure had stabilized (whichever was longer.) The high pressure liquid chromatography pump was then started, feeding a mixture consisting of 70 weight percent methanol and 30 weight percent methyl iodide at a rate of 12 ml/hr (The solution had a density of 1 g/mL.) Samples of the liquid product were collected and analyzed periodically using gas chromatographic techniques.

Example 1

Catalyst 1, the gold-on-carbon catalyst, was used in the Carbonylation of Methanol procedure described above. The composition and weight of the samples taken periodically during the carbonylation are set forth in Table 1. As used in Table 1, "Time" is the total time of operation (in hours) of the carbonylation, commencing with the feeding of the methanol until a particular sample aliquot was withdrawn. The values set forth below "MeI" (methyl iodide), "MeOAc" (methyl acetate), "MeOH" (methanol) and "HOAc" (acetic acid) are the weight percentages of each of those compounds present in the sample. The weight of each sample is given in grams.

TABLE 1

| Sample Number | Expired Time (h) | Wt % MeI | Wt % MeOAc | Wt. % MeOH | Wt % HOAc | Sample Weight (g) |
|---|---|---|---|---|---|---|
| 1 | 3.00 | 20.4 | 1.09 | 72.92 | 0 | 35.8 |
| 2 | 7.00 | 20.32 | 1.12 | 71.72 | 0 | 48.6 |
| 3 | 10.00 | 19.49 | 1.13 | 73.55 | 0 | 36.8 |
| 4 | 15.00 | 21.63 | 1.69 | 68.92 | 0 | 61.2 |
| 5 | 17.50 | 21.55 | 1.62 | 69.35 | 0 | 28.1 |
| 6 | 23.00 | 21.6 | 1.64 | 69.92 | 0 | 73.1 |
| 7 | 27.00 | 21.9 | 4.64 | 68.6 | 0 | 48.1 |
| 8 | 31.00 | 22.05 | 4.63 | 67.9 | 0 | 48.5 |
| 9 | 34.00 | 22.59 | 4.64 | 68.46 | 0 | 36.9 |
| 10 | 39.00 | 22 | 4.52 | 67.83 | 0 | 62.1 |
| 11 | 41.50 | 21.19 | 12.23 | 60.47 | 0 | 25.3 |
| 12 | 47.00 | 21.45 | 12.17 | 60.85 | 0 | 73.1 |
| 13 | 51.00 | 19.07 | 15.57 | 54.42 | 0.33 | 47.8 |
| 14 | 55.00 | 20.43 | 16.55 | 57.34 | 0.37 | 49.1 |
| 15 | 58.00 | 18.28 | 15.69 | 55.75 | 0.39 | 36.9 |
| 16 | 63.00 | 17.81 | 21.31 | 47.4 | 0.85 | 62.1 |
| 17 | 65.50 | 18.66 | 21.54 | 48.22 | 0.77 | 28.1 |
| 18 | 71.00 | 17.87 | 21.44 | 47.61 | 0.85 | 71.1 |
| 19 | 75.00 | 18.31 | 22.42 | 44.75 | 1 | 49.3 |
| 20 | 79.00 | 17.9 | 23.09 | 46.93 | 1.21 | 48.6 |

The rate of acetyl production based on the preceding experiment utilizing Catalyst 1 is set forth in table 2, wherein Sample Number and Time values correspond to those of Table 1. "Acetyl Produced" is the amount (millimoles) of methyl acetate and acetic acid produced during each increment of Time calculated from the formula:

$$\text{Sample Weight} \times 10 \times ((\text{weight \% MeOAc}/74) + (\text{weight \% AcOH}/60))$$

"Production Rate" is the moles of Acetyl Produced per liter of catalyst volume per hour during each increment of Time (Time Increment), i.e., the time of operation between samples. The formula for determining moles of Acetyl Produced per liter of catalyst volume per hour is:

$$(\text{Acetyl Produced}/(0.5 \times \text{Time Increment})) \times 0.57,$$

wherein 0.5 is the grams of catalyst used and 0.57 is the density of the catalyst in g/mL.

TABLE 2

| Sample Number | Expired Time (h) | Acetyl Produced (mmol) | Rate (mol/L-h) |
|---|---|---|---|
| 1 | 3.00 | 5.3 | 2.0 |
| 2 | 7.00 | 7.4 | 2.1 |
| 3 | 10.00 | 5.6 | 2.1 |
| 4 | 15.00 | 14.0 | 3.2 |
| 5 | 17.50 | 6.2 | 2.8 |
| 6 | 23.00 | 16.2 | 3.4 |
| 7 | 27.00 | 30.2 | 8.6 |
| 8 | 31.00 | 30.3 | 8.6 |
| 9 | 34.00 | 23.1 | 8.8 |
| 10 | 39.00 | 37.9 | 8.6 |
| 11 | 41.50 | 41.8 | 19.1 |
| 12 | 47.00 | 120.2 | 24.9 |
| 13 | 51.00 | 103.2 | 29.4 |
| 14 | 55.00 | 112.8 | 32.2 |
| 15 | 58.00 | 80.6 | 30.6 |
| 16 | 63.00 | 187.6 | 42.8 |
| 17 | 65.50 | 85.4 | 38.9 |
| 18 | 71.00 | 216.1 | 44.8 |
| 19 | 75.00 | 157.6 | 44.9 |
| 20 | 79.00 | 161.4 | 46.0 |

Upon reaching the maximum rate (i.e. over the last 5 samples) the selectivity for acetyls is >97%, when calculated as:

$$\text{Selectivity} = \frac{\text{moles of acetyl produced}}{\text{moles equivalents of MeOH consumed} + \text{moles of MeI consumed}} \times 100\%$$

where, mole of acetyl produced=mol of AcOH in product +mole of MeOAc in product mole equivalents of MeOH consumed=mol of MeOH fed−mol of MeOH in product−mol of MeOAc in product and moles of MeI consumed=mol of MeI fed−moles of MeI in product.

Example 1 was repeated twice to verify the results. Each of the two repeat examples demonstrated the same behavior observed above in that they were characterized by:

a) an induction period of very low activity lasting 18–28 hours followed by, b) a period of increasing activity lasting approximately an additional 20–30 hours, and c) finally achieving a final steady state rate of approximately 45 mol of acetyl/$L_{cat}$-h (80 mol of acetyl/$kg_{cat}$-h).

In each case, even higher (>99%) selectivity for acetyls was observed upon reaching the final steady state rate.

Example 2

(Comparative C-1)

The sample 1 was repeated using Comparative Catalyst C-1 (Ag on carbon). The results are shown below in Table 3 and Table 4. The calculations used to generate the information in Table 3 and 4 are identical to those used in Example 1.

TABLE 3

Carbonylation with a Silver-on-Carbon Catalyst

| Sample Number | Expired Time (h) | Wt % MeI | Wt % MeOAc | Wt. % MeOH | Wt % HOAc | Sample Weight (g) |
|---|---|---|---|---|---|---|
| 1 | 3.00 | 16.22 | 1.82 | 73.12 | 0.23 | 36.3 |
| 2 | 7.00 | 15.72 | 1.76 | 71.96 | 0.21 | 48.9 |
| 3 | 10.00 | 15.72 | 1.76 | 72.42 | 0.17 | 37.3 |
| 4 | 15.00 | 15.29 | 1.86 | 72.72 | 0.22 | 62.3 |
| 5 | 17.50 | 15.38 | 0.68 | 74.44 | 0 | 25.1 |
| 6 | 23.00 | 14.83 | 0.63 | 75.74 | 0 | 70.8 |
| 7 | 25.00 | 16.01 | 0.63 | 73.06 | 0 | 49.1 |
| 8 | 27.00 | 17.13 | 1.6 | 70.6 | 0 | 48.5 |
| 9 | 29.00 | 17.31 | 1.49 | 69.71 | 0 | 37.9 |
| 10 | 31.00 | 17.09 | 1.38 | 70.53 | 0 | 25.1 |
| 11 | 33.00 | 16.37 | 1.61 | 74.86 | 0 | 24.9 |
| 12 | 35.00 | 16.09 | 1.65 | 74.14 | 0 | 24.7 |
| 13 | 39.00 | 14.92 | 1.49 | 73.88 | 0 | 49.8 |
| 14 | 41.00 | 15.76 | 1.78 | 75.34 | 0 | 25.2 |
| 15 | 47.00 | 18.69 | 2.63 | 71.85 | 0.27 | 71.9 |
| 16 | 51.00 | 17.6 | 2.64 | 72.27 | 0.21 | 49.1 |
| 17 | 55.00 | 18.28 | 2.6 | 74.03 | 0.2 | 48.8 |
| 18 | 58.00 | 17.32 | 2.69 | 75.06 | 0.22 | 37.2 |
| 19 | 63.00 | 16.83 | 2.58 | 76.7 | 0.21 | 62.2 |
| 20 | 65.00 | 16.09 | 2.63 | 75.21 | 0.2 | 25.3 |

TABLE 4

| Sample Number | Expired Time (h) | Acetyl Produced (mmol) | Rate (mol/L-h) |
|---|---|---|---|
| 1 | 3.00 | 10.3 | 3.9 |
| 2 | 7.00 | 13.3 | 3.8 |
| 3 | 10.00 | 9.9 | 3.8 |
| 4 | 15.00 | 17.9 | 4.1 |
| 5 | 17.50 | 2.3 | 1.1 |
| 6 | 23.00 | 6.0 | 1.2 |
| 7 | 25.00 | 4.2 | 2.4 |
| 8 | 27.00 | 10.5 | 6.0 |
| 9 | 29.00 | 7.6 | 4.3 |
| 10 | 31.00 | 4.7 | 2.7 |
| 11 | 33.00 | 5.4 | 3.1 |
| 12 | 35.00 | 5.5 | 3.1 |
| 13 | 39.00 | 10.0 | 2.9 |
| 14 | 41.00 | 6.1 | 3.5 |
| 15 | 47.00 | 28.8 | 5.5 |
| 16 | 51.00 | 19.2 | 5.5 |
| 17 | 55.00 | 18.8 | 5.4 |
| 18 | 58.00 | 14.9 | 5.7 |
| 19 | 63.00 | 23.9 | 5.4 |
| 20 | 65.00 | 9.8 | 5.6 |

As can be readily discerned from the above data, silver is a very poor catalyst for the carbonylation of methanol, when compared to gold.

Example 3

(Comparative C-2)

Carbonylation Example 1 was repeated using Comparative Catalyst 2 (Ir on carbon) instead of the gold on carbon catalyst. There was no induction period and the catalyst produced 8.65 moles of acetyl product over a period of 178 hours with a selectivity toward acetyl products of 96%. This corresponds to a rate of 55 mol/L-h. This comparative example shows that the gold on carbon catalyst compares favorably (showing similar rates) to that for an iridium based catalyst.

Although the present invention has been described in terms of the presently preferred embodiment, it is to be understood that such disclosure is not to be interpreted as limiting to the invention described herein. No doubt that after reading the disclosure, various alterations and modifications will become apparent to those skilled in the art to which the invention pertains. It is intended that the appended claims be interpreted as covering all such alterations and modifications as fall within the spirit and scope of the invention.

We claim:

1. A catalyst useful in a vapor-phase carbonylation process, comprising a catalytically effective amount of gold associated with a solid catalyst support, and a vapor-phase halide promoter selected from the group consisting of chlorine compounds, bromine compounds, iodine compounds, and mixtures thereof, wherein said catalyst is substantiallly free of iridium, rhodium, and nickel.

2. The catalyst of claim 1 wherein said support is selected from the group consisting of carbon, activated carbon, pumice, alumina silica, silica-alumina, magnesia, diatomaceous earth, bauxite, titania, zirconia, clay, magnesium, silicate, silicon carbide, zeolites, ceramics and combinations thereof.

3. The catalyst of claim 2 wherein said solid support is carbon.

4. The catalyst of claim 2 wherein said solid support is activated carbon.

5. The catalyst of claim 1 wherein said gold is a gold compound selected from the group consisting of gold halides, cyanides, hydroxides, oxides, sulfides, phosphine complexes, salts thereof, and mixtures thereof.

6. The catalyst of claim 1 wherein said catalyst comprises from about 0.01 weight percent to about 10 weight percent of said gold.

7. The catalyst of claim 6 wherein said catalyst comprises from about 0.1 weight percent to about 2 weight percent of said gold.

8. The catalyst of claim 1 wherein said catalyst comprises said gold and another metal selected from the group consisting of alkaline metals, alkaline earth metals, lanthanides, tin, vanadium molybdenum, tungsten, and combinations thereof.

9. The catalyst of claim 8 wherein the weight ratio of said gold to said metal is greater than 1:1.

10. The catalyst of claim 1 wherein said halide promoter is selected from the group consisting of hydrogen halides, alkyl halides having up to 12 carbon atoms, aryl halides having up to 12 carbon atoms, molecular halides, and mixtures thereof.

11. The catalyst of claim 10 wherein said halide promoter is selected from the group consisting of hydrogen halides and alkyl halides having up to 6 carbon atoms.

12. The catalyst of claim 11 wherein said halide promoter is selected from the group consisting of hydrogen iodide, gaseous hydridic acid, methyl iodide, ethyl iodide, 1-iodopropane, 2-iodobutane, 1-iodobutane, hydrogen bromide, methyl bromide, ethyl bromide, benzyl iodide, and mixtures thereof.

13. A catalyst useful for producing acetic acid, methyl acetate or a mixture thereof in a vapor-phase carbonylation process, said catalyst comprising from about 0.01 weight percent to about 10 weight percent of gold associated with a solid catalyst support material, and a halide promoter selected from the group consisting of chlorine compounds, bromine compounds, iodine compounds, and mixtures thereof, wherein said catalyst is substantially free of iridium, rhodium, and nickel.

14. The catalyst of claim 13 wherein said catalyst comprises from about 0.1 weight percent to about 2 weight percent of said gold.

15. The catalyst of claim 13 wherein said halide promoter is in a vapor phase.

16. The catalyst of claim 13 wherein said halide promoter is selected from the group consisting of hydrogen halides, alkyl halides having up to 12 carbon atoms, aryl halides having up to 12 carbon atoms, molecular halides, and mixtures thereof.

17. The catalyst of claim 16 wherein said halide promoter is selected from the group consisting of hydrogen halides and alkyl halides having up to 6 carbon atoms.

18. The catalyst of claim 17 wherein said halide promoter is selected from the group consisting of hydrogen iodide, gaseous hydriodic acid, methyl iodide, ethyl iodide, 1-iodopropane, 2-iodobutane, 1-iodobutane, hydrogen bromide, methyl bromide, ethyl bromide, benzyl iodide, and mixtures thereof.

* * * * *